United States Patent
Wilson

(10) Patent No.: US 7,133,496 B2
(45) Date of Patent: Nov. 7, 2006

(54) SOFT TISSUE CEPHALOMETRIC SCREEN WITH SUBMENTAL-NECK EXTENSION, AND RADIOLOGY APPARATUS, MODULAR SYSTEM AND IMAGING METHOD USING SAME

(75) Inventor: David G. Wilson, Selinsgrove, PA (US)

(73) Assignee: David G. Wilson, D.M.D., LLC, Selinsgrove, PA (US)

( * ) Notice: Subject to any disclaimer, the term of this patent is extended or adjusted under 35 U.S.C. 154(b) by 140 days.

(21) Appl. No.: 10/796,450

(22) Filed: Mar. 9, 2004

(65) Prior Publication Data

US 2005/0201522 A1 Sep. 15, 2005

(51) Int. Cl.
*G21K 3/00* (2006.01)

(52) U.S. Cl. ......................... 378/156; 378/38
(58) Field of Classification Search ................ 378/38, 378/39, 40, 156, 157, 158, 159, 168, 147, 378/204, 205, 206
See application file for complete search history.

(56) References Cited

U.S. PATENT DOCUMENTS

| | | | |
|---|---|---|---|
| 3,819,937 A | 6/1974 | Sovijarvi et al. | 378/158 |
| 4,082,957 A | 4/1978 | Morlan | 378/156 |
| 4,163,902 A | 8/1979 | Musaph | 378/147 |
| 4,641,336 A | 2/1987 | Gastrin | 378/156 |
| 5,016,264 A | 5/1991 | Hyttinen | 378/38 |
| 5,425,065 A | 6/1995 | Jarvenin | 378/40 |
| 5,444,754 A | 8/1995 | Wederhorn et al. | 378/38 |
| 5,454,023 A * | 9/1995 | Asikainen | 378/156 |
| 6,466,641 B1 | 10/2002 | Virta et al. | 378/38 |

OTHER PUBLICATIONS

Soft tissue filter screen for the Wehmer collimator first used circa 1984, illustrated in Figure 1 attached.
Soft tissue filter x-ray cassette adaptor publicly available since 1976, illustrated in Figure 2 attached.
TP Laboratories soft tissue face shield on sale as of 1979, illustrated in Figure 3 attached.
Brochure from Instrumentation Imaging, Inc., Title of the brochure is Orthopantomograph OP 100 Advanced Dental Imaging, 1998, pertinent page is p. 6, Instrumentarium Corp. Imaging Division, Tuusula, Finland.

* cited by examiner

*Primary Examiner*—Edward J. Glick
*Assistant Examiner*—Courtney Thomas
(74) *Attorney, Agent, or Firm*—RatnerPrestia

(57) ABSTRACT

An apparatus for use in a cephalostat has a collimator for defining the shape of an X-ray beam and a soft tissue filter screen, mounted independently of the collimator, for attenuating a portion of the X-ray beam. The soft tissue filter screen has an anterior facial portion and a submental-neck portion having a leading edge at a position posterior relative to the leading edge of the anterior facial portion. The soft tissue filter screen is independently adjustable relative to the collimator. A cephalometric radiology apparatus includes a support structure, an X-ray source, and an X-ray detector, in addition to the collimator and the soft tissue filter screen. A method for imaging soft tissue and hard tissue involves positioning the soft tissue filter independently of positioning the collimator. A modular system, which can be mounted onto a cephalostat, includes the soft tissue filter screen and a mounting component.

34 Claims, 17 Drawing Sheets

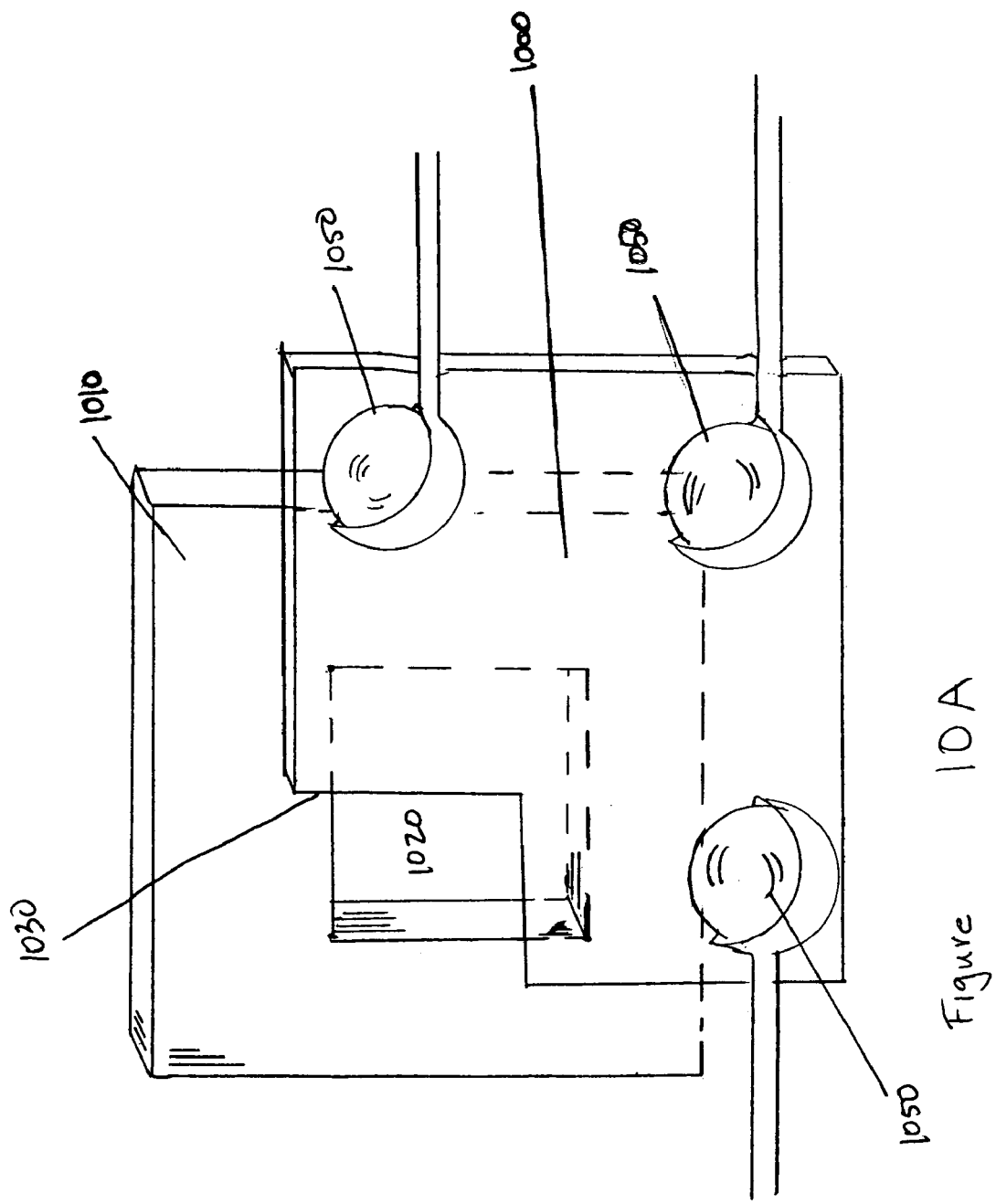

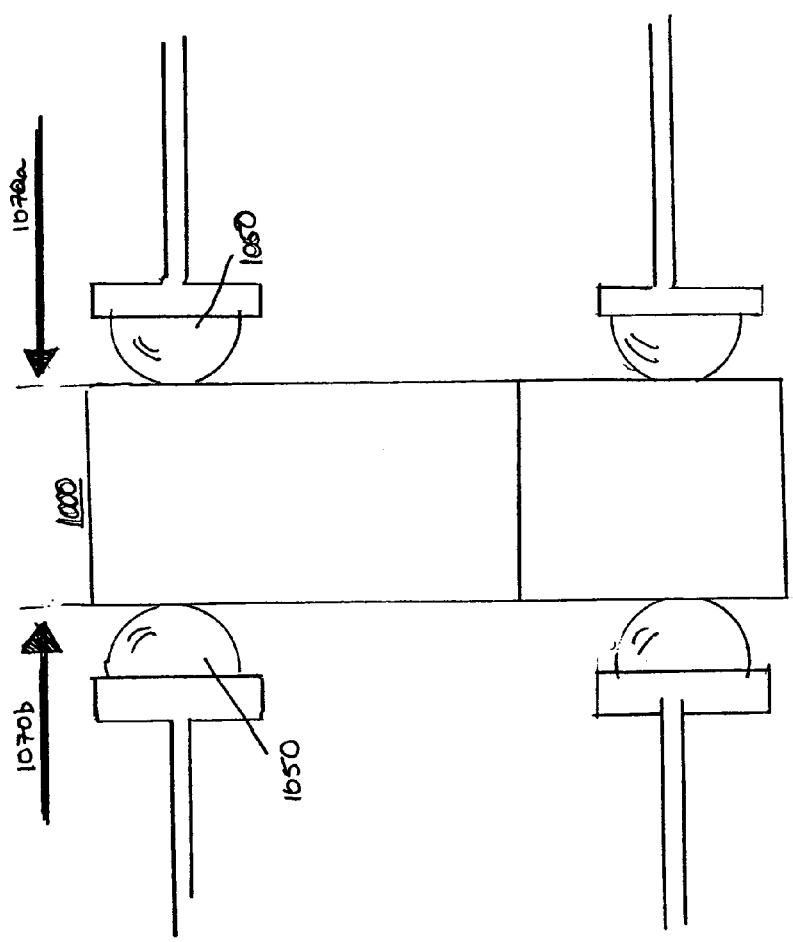

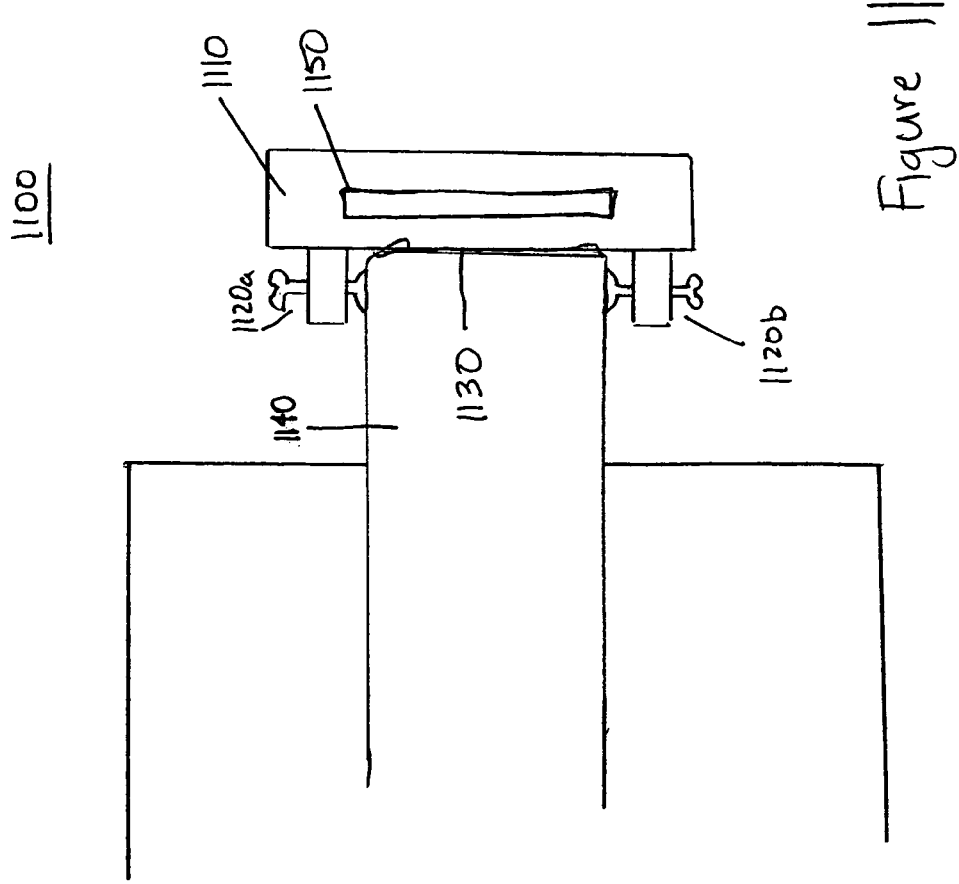

SOFT TISSUE CEPHALOMETRIC SCREEN WITH SUBMENTAL-NECK EXTENSION, AND RADIOLOGY APPARATUS, MODULAR SYSTEM AND IMAGING METHOD USING SAME

FIELD OF THE INVENTION

This invention pertains to cephalometric radiographic images and systems and devices used to take such images. More specifically, this invention pertains to a cephalometric radiographic image of the soft tissue submental-neck region in addition to the anterior facial region of a patient's head for use in diagnostic and treatment purposes.

BACKGROUND OF THE INVENTION

Treatment for patients requiring orthodontic/orthopedic, orthognathic, or facial plastic surgery should include a cephalometric analysis of soft tissues. As used herein, soft tissue refers to those tissues that are less dense than bone, cartilage, and teeth, herein referred to as hard tissues. Examples of soft tissue include skin, lips, muscles and tendons.

One analysis of soft tissue cephalometric landmarks is described in Legan, et al., *Soft Tissue Cephalometric Analysis for Orthognathic Surgery*, J. Oral Surgery, Vol. 38, p.744–751 (October, 1980), herein incorporated by reference. Soft tissue landmarks are used to identify facial relationships, while hard tissue landmarks are used to evaluate tooth and boney relationships. Together, the soft tissue and hard tissue findings are used to establish a treatment guidance for the dentition and supporting structures to attain and maintain optimum relations in physiologic and esthetic harmony among facial and cranial structures. The soft tissue cephalometric landmarks are most important when trying to achieve desirable facial esthetics through orthodontic/orthopedic treatment, orthognathic surgery or facial plastic surgery.

FIG. 1 shows a schematic profile of a human head. Soft tissue details such as the nose, the lips, the chin, the throat and the neck as well as hard tissue structures of the chin, maxilla and mandible, occipital bone and sphenoid bone are shown. Reference numeral 100 designates a predominantly soft tissue area defined herein as the anterior facial portion. This area includes the soft tissue of the forehead, nose, lips and chin. Reference numeral 120 designates a predominantly soft tissue area defined herein as the submental-neck portion. This area includes the facial soft tissue inferior to the mandible and neck contour of a patient. Reference numeral 130 designates predominantly the soft tissue portion of the lower neck. At the intersection of submental-neck portion 120 and lower neck portion 130 is the cervical point 140. The contour of the submental-neck portion and lower neck portion is an important consideration in the esthetic look of a patient. As used herein, the contour of a patient's neck is that portion of the soft tissue extending from the chin, through the submental-neck portion 120, across cervical point 140, and extending into at least part of the lower neck portion 130 of the patient.

Numerous devices attempt to image the above-described soft tissue as well as hard tissue on the same radiograph. Referring now to FIG. 2A, a soft tissue filter screen having a straight vertical edge (i.e., an edge adapted to extend in the superior/inferior direction) has been used in connection with a cephalostat. FIG. 2A shows area 200 of a patient's head corresponding to attenuated X-rays that have passed through a prior art soft tissue filter. With this soft tissue filter screen, only the soft tissue of the anterior facial portion of a patient's head is imaged on the resulting radiograph. FIG. 2B is the radiograph of a patient's head taken with a cephalostat using the soft tissue filter screen reflected in FIG. 2A. This screen having a vertical edge across the entire height of the imaged area fails to attenuate X-rays passing through the submental-neck portion and lower neck portion of the patient's head. The resulting radiograph shows a darkened overexposed area where the patient's neck line would be.

One attempted solution to view the anterior facial portion and the submental-neck portion of a patient's head on the same radiograph would be to widen the soft tissue filter screen. FIG. 3A shows a reflection of a wide soft tissue filter screen with reference numeral 300 designating the area of the patient's head corresponding to attenuated X-rays from the soft tissue filter screen. A problem with widening the soft tissue filter screen is that the filter then blurs hard tissue landmarks. FIG. 3B is a radiograph of a patient's head taken with a cephalostat using a wide soft tissue screen. Line 310 marks the posterior edge of the soft tissue filter. As can been seen, only a part of the submental-neck portion has been imaged, the hard tissue landmarks around the teeth have been blurred and still, the cervical point and all of the neck contour is not visible.

A different approach to solving the problem of visualization of the soft tissue of the anterior facial and submental-neck portion (and possibly the lower neck portion) congruently with hard tissue structures on the same radiograph is through the use of a face shield. Shown in FIG. 4A is a hand-held face shield 400 contoured to a patient's face. One disadvantage of this type of face shield is that each patient's face is uniquely shaped and many different sized face shields would be needed. Secondly, the face shield must be held in place by the patient. The clarity of the radiograph depends upon how steady a patient can hold the face shield against his face. In this regard, the face shield is impractical for use with young children. Yet a further drawback to the face shield shown in FIG. 4A is that it imparts a drastic line of demarcation on the radiograph from the leading edge 410 of face shield 400. FIG. 4B shows a radiograph of a patient's head using the face shield 400. Demarcation line 420 is clearly visible, and hard tissue blurring of the front teeth and anterior boney landmarks still occurs.

What is needed therefore is an adaptable system for attenuating X-ray energy over soft tissue cephalometric landmarks of the anterior facial portion and submental-neck portion of a patient's head while maintaining the X-ray energy over hard tissue landmarks permitting imaging of both soft and hard tissue landmarks on the same radiograph.

SUMMARY OF THE INVENTION

An embodiment of the present invention pertains to an apparatus for use in a cephalostat comprising a collimator for defining the shape of an X-ray beam and a soft tissue filter screen for attenuating a portion of the X-ray beam. The soft tissue filter screen has an anterior facial portion and a submental-neck portion, each having a leading edge. The leading edge of the anterior facial portion is located at the most posterior position of the anterior facial portion. The leading edge of the submental-neck portion has a leading edge at a position posterior relative to the leading edge of the anterior facial portion. The soft tissue filter screen is independently adjustable relative to the collimator.

Another embodiment of the present invention pertains to a cephalometric radiology apparatus comprising a support structure, an X-ray source, a collimator, a soft tissue filter screen, and an X-ray detector. The X-ray source is supported by the support structure and serves to emit X-rays. The collimator is supported by the support structure and is positioned along the path of the X-rays for defining an X-ray beam emitted from the X-ray source. The soft tissue filter screen includes an anterior facial portion and a submental-neck portion as described above. The X-ray detector collects X-rays emitted from the X-ray source.

The present invention also pertains to a method for imaging soft tissue and hard tissue congruently on the same radiograph. The method comprises the steps of emitting X-rays from an X-ray source, positioning a collimator, positioning a soft tissue filter screen, and collecting the X-rays on a radiograph. The collimator is positioned across the X-rays to define an X-ray beam. The soft tissue filter screen is positioned independently of the step of positioning the collimator and attenuates X-rays passing through the tissue of the forehead, nose, lips, chin and neck of a patient. The soft tissue filter screen has an anterior facial portion and a submental-neck portion as described above.

Still another embodiment of the present invention pertains a modular soft tissue filter screen system for use with a cephalostat having a collimator. The soft tissue filter screen system has a soft tissue filter screen for attenuating a portion of an X-ray beam and a mounting component. The soft tissue filter screen has an anterior facial portion and a submental-neck portion, as described above. The mounting component serves to support the soft tissue filter screen and is adapted to be attached to the cephalostat at a position such that the soft tissue filter screen is aligned within the X-ray beam.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 10A is a partial perspective view and partial schematic view showing aspects of a soft tissue filter screen according to the present invention.

FIG. 10B is a partial side view and partial schematic view of a soft tissue filter screen according to the present invention.

FIG. 11 schematic view of a modular soft tissue filter screen system according to an embodiment of the present invention and a portion of a cephalostat to which the system is attached.

DETAILED DESCRIPTION OF THE INVENTION

Figure 8:
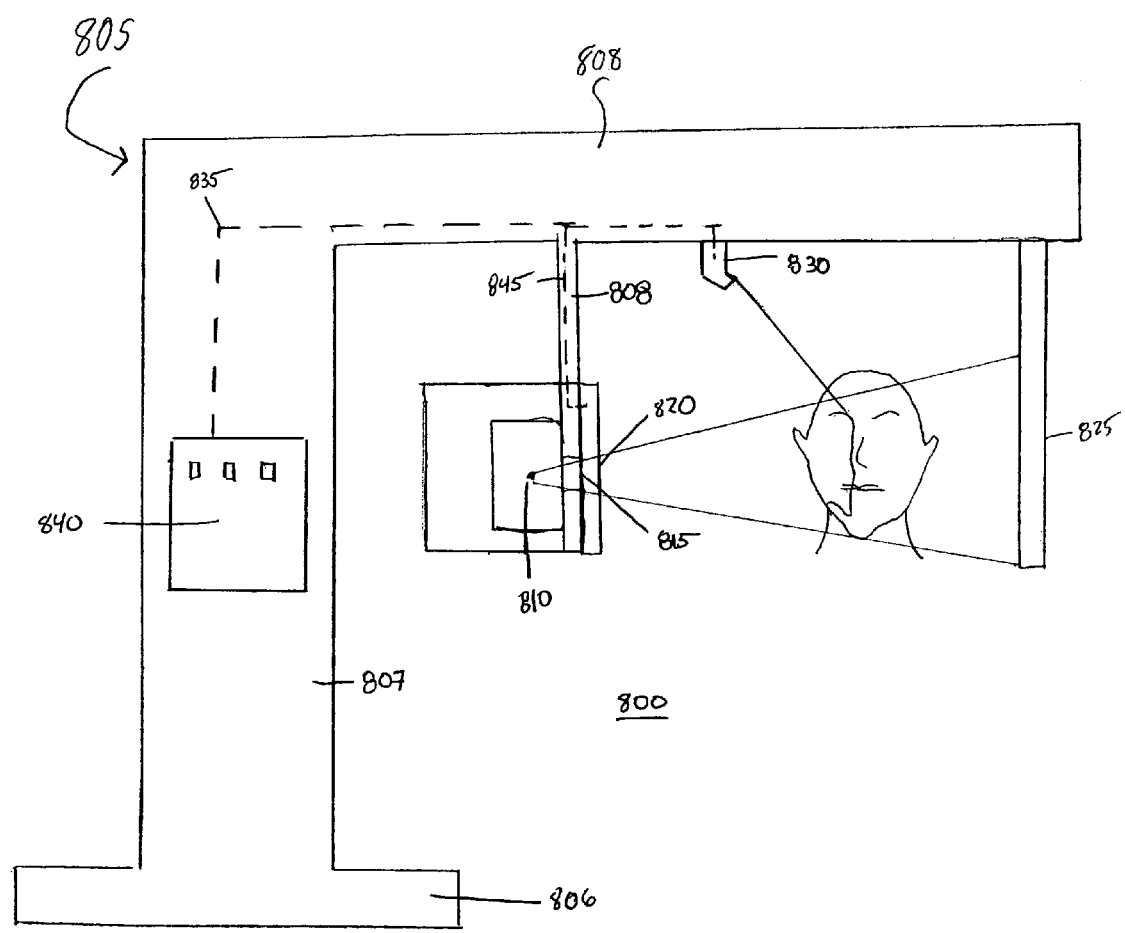
FIG. 8 is a schematic view of a cephalometric radiology apparatus according to the present invention.

FIG. 8 shows a cephalometric radiology apparatus 800 according to the present invention. Cephalometric radiology apparatus 800, commonly referred to as an x-ray machine, comprises a support structure 805, an x-ray source 810, a collimator 815, a soft tissue filter screen 820, and an x-ray detector 825. Cephalometric radiology apparatus may be used to take cephalometric radiographs of a patient's head as well as other types of radiographs derived from the Sub-mento-Vertex, Water's view and Towne's view techniques. As shown, support structure 805 comprises a base 806 for being placed on the floor, a column 807, and an arm 808 extending from the top of the column. Other support structures in connection with the present invention may be used, for example, support structures of other configurations, which may be wall mounted, or support structures made up of individual components. Thus, the other components of the cephalometric radiology apparatus 800 can be connected to a single unitary support structure as shown in FIG. 8 or individual components of a support structure. As used herein, the term "support structure" shall be deemed to encompass these various embodiments.

X-ray source 810 as shown in FIG. 8 is supported by support structure 805 and serves to emit X-rays. X-ray source 810 is shown as connected to arm 808, but may be connected to column 807, base 806 or wall mounted. X-ray source 810 may be any conventional x-ray source used for radiographic imagery.

Collimator 815 shown in FIG. 8 is supported by support structure 805 and positioned along the path of the X-rays that are emitted from X-ray source 810. Collimator 815 is the X-ray beam-limiting device. In a known manner, collimator 815 intercepts divergent X-rays so that a parallel X-ray beam is directed through a patient's head onto X-ray detector 825. As shown in FIG. 8, a single collimator is placed adjacent X-ray source 810. Alternatively, more than one collimator may be used. The collimator may be placed adjacent to the X-ray source as shown in FIG. 8 or may be placed at a position away from the X-ray source. In either embodiment, the collimator serves to confine the X-rays into a defined beam.

Figure 9A:
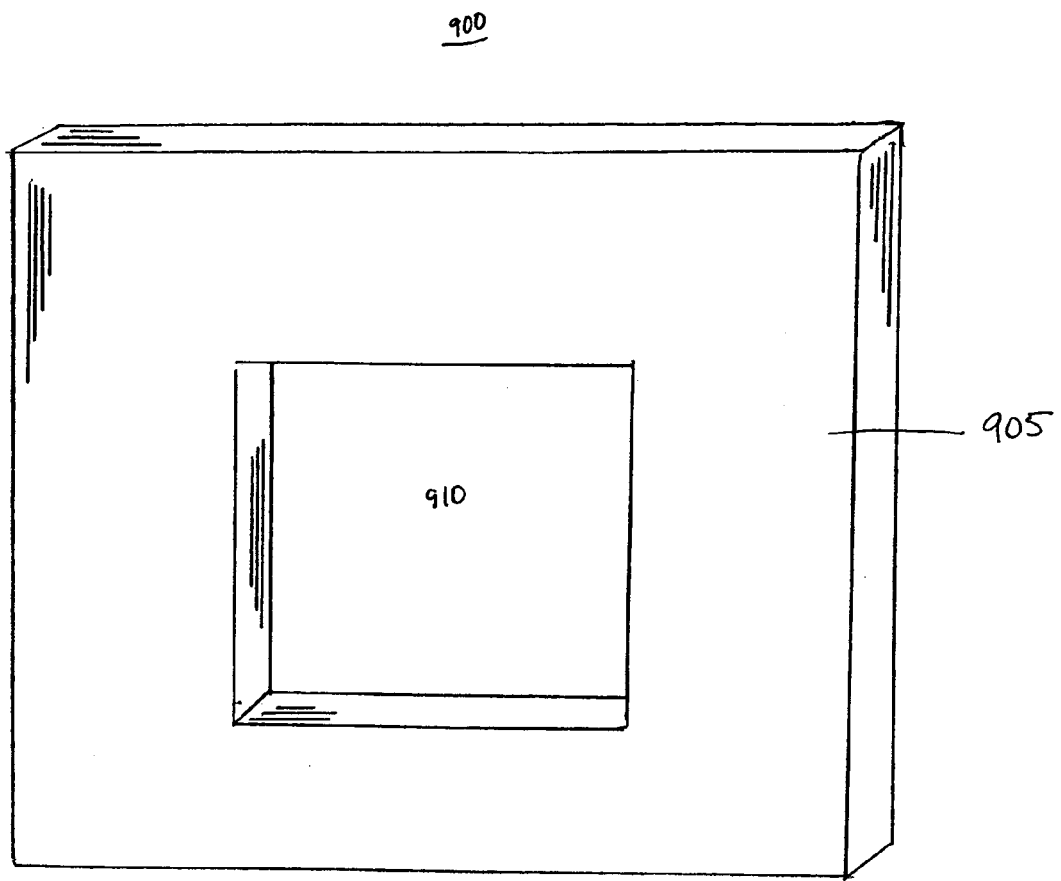
FIG. 9A is a perspective view of a collimator which can be used in connection with the present invention.
Figure 9B:
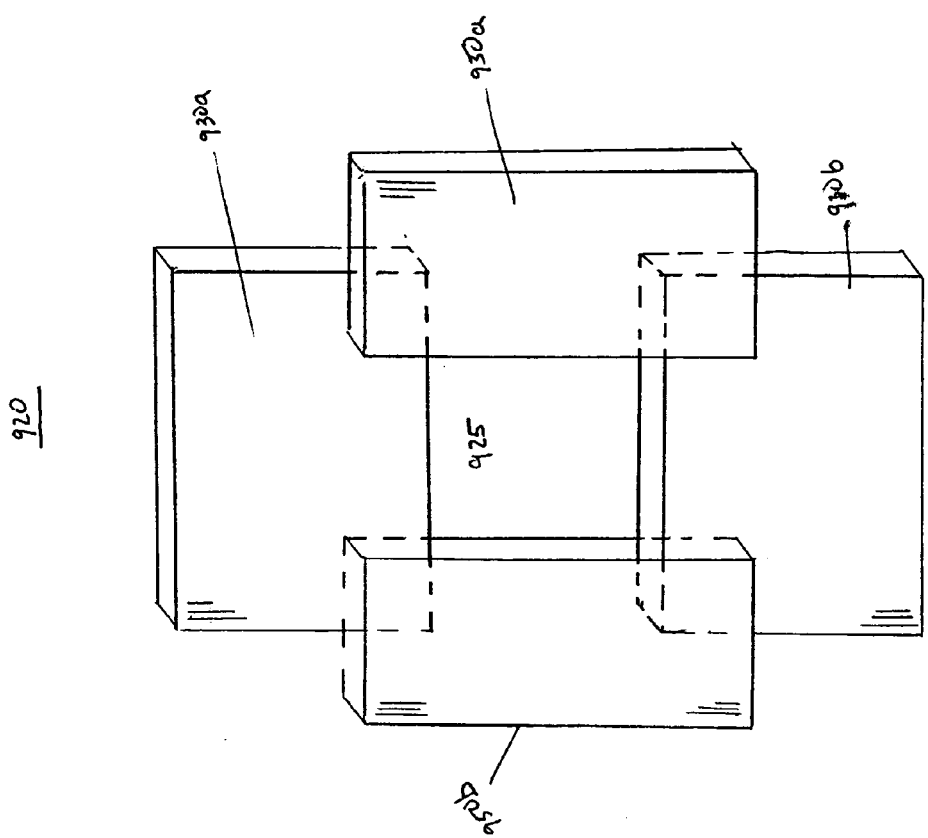
FIG. 9B is a perspective view of another collimator which can be used in connection with the present invention.

According to an alternative embodiment, collimator 815 may be a simple aperture or diaphragm. Collimator 815 may be a plate defining a small hole. The size and shape of the hole determines the size and shape of the X-ray beam. FIG. 9A shows one embodiment of the collimator used in the cephalometric radiology device 800 of FIG. 8 as an aperture or diaphragm collimator 900. Aperture or diaphragm collimator 900 may be a single frame 905 defining an opening 910 that defines the X-ray beam emitted from the X-ray source. In an alternative embodiment shown in FIG. 9B, the collimator is modular (i.e., is made up of multiple components). FIG. 9B shows a modular collimator 920 defining opening 925 according to another embodiment of the present invention. In this embodiment, modular collimator 920 has plates 930a, 930b positioned off-plane relative to plates 950a, 950b. In another embodiments, plates 930a, 930b and 950a, 950b may be located on the same plane, in which case the plates may be slotted to intermesh. Plates 930a, 930b are movable in the vertical direction and plates 950a, 950b are movable in the horizontal direction. In this manner, plates 930a, 930b and 950a, 950b define an opening to define the X-ray beam and are independently adjustable relative to one another towards and away from the center of opening 925. While four rectangular plates are shown in modular collimator 920, any number of plates of any shape or size may be used to define the opening or an iris may be used to define the opening.

Figure 5:
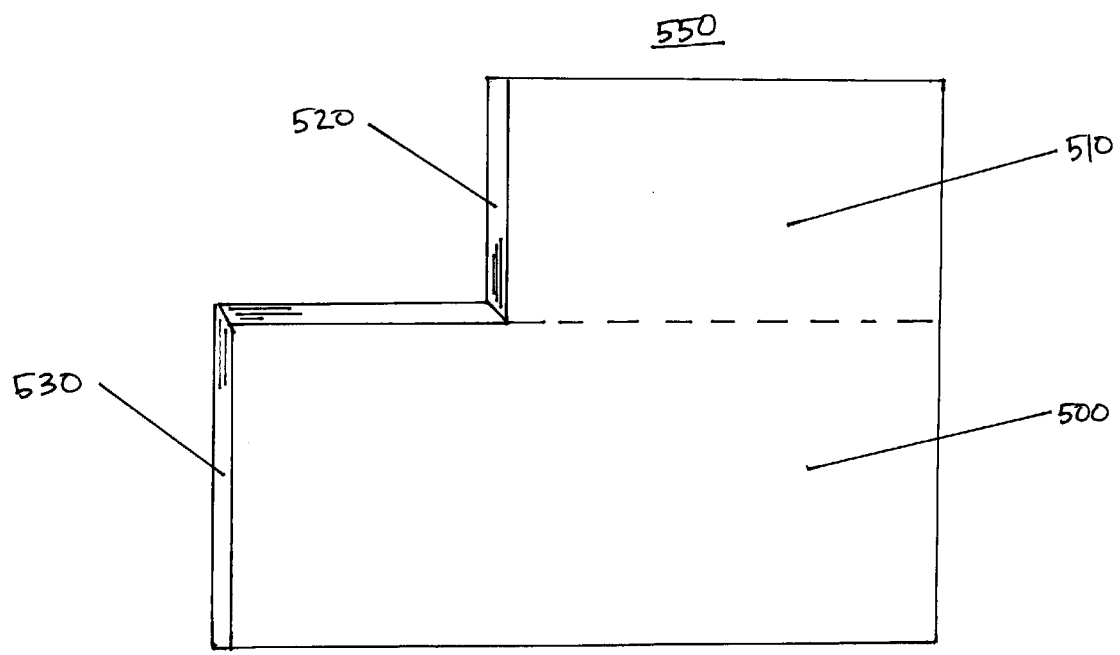
FIG. 5 is a schematic view of a soft tissue filter screen according to an embodiment of the present invention.

Referring now to FIG. 8, the soft tissue filter screen 820 is mounted between collimator 815 and the patient's head. Alternatively, soft tissue filter screen 820 may be mounted between X-ray source 810 and collimator 815. Shown in FIG. 5 is one embodiment of soft tissue filter screen 550 according to the present invention. Soft tissue filter screen 550 is L-shaped having a first leg and a second leg disposed perpendicular to one another. The first leg of soft tissue filter screen 550 is an 25 anterior facial portion 510. The second leg of soft tissue filter screen 550 is a submental-neck portion 500. It should be pointed out that, in use, only a portion of the left-hand side of the soft tissue filter screen 550 is actually used to attenuate X-rays, thus the "L" shape can be easily visualized. The soft tissue filter screen of the present invention may be made of any suitable X-ray attenuating material. Preferably, the soft tissue filter screen is copper.

Anterior facial portion 510 has a leading edge 530 located at the most posterior position of the anterior facial portion. As used herein, the term anterior and posterior mean a direction, within the two-dimensional plane of a face of the soft tissue filter screen, parallel to the direction to and from a patient's nose straight to the back of the head when apparatus 800 is in use. Similarly, the terms inferior and superior mean a direction, within the two-dimensional plane of a face of the soft tissue filter screen, parallel to the direction to and from the top and bottom of a patient's head when apparatus 800 is in use. As can be seen FIG. 8, a patient is positioned between X-ray source 810 and X-ray detector 825. The patient is positioned such that the X-ray beam passes through the side of the patient's head. In this manner, when the soft tissue filter screen is moved in a horizontal direction, the leading edge of the soft tissue filter screen will travel in a direction from the patient's nose to the back of the head.

Figure 7A:
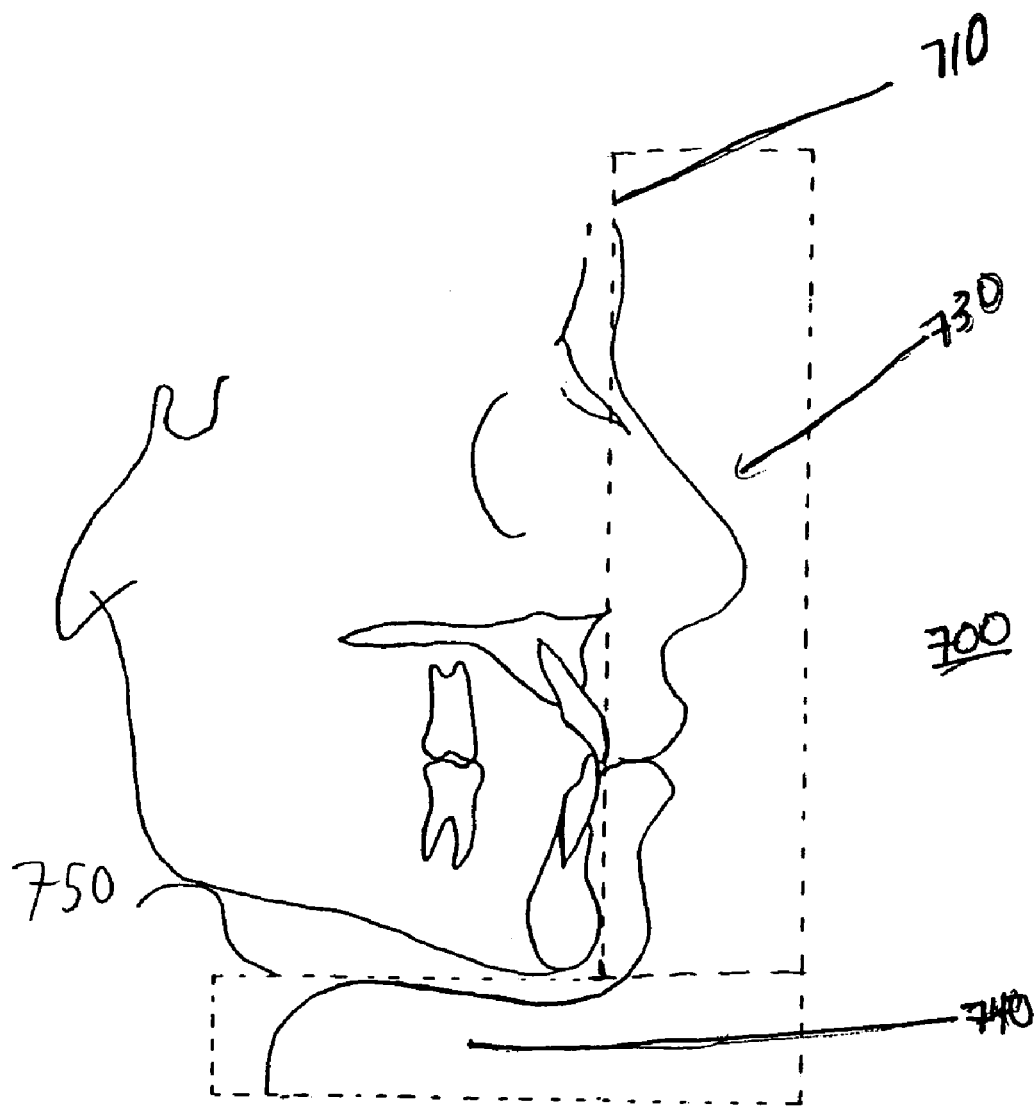
FIG. 7A is a schematic view of the area of a patient's head exposed to X-rays attenuated by a soft tissue filter screen according to the present invention.

FIG. 7A shows the area 700 of a patient's head exposed by attenuated X-rays using one embodiment of the soft tissue filter screen of the present invention. Line 710 corresponds to the leading edge of anterior facial section 510 of soft tissue filter screen 550 shown in FIG. 5. Therefore, as used herein, the anterior/posterior direction in relation to the patient's head is the same as the horizontal direction in relation to moving the soft tissue filter screen in the path of the X-ray beam. Likewise, as used herein the inferior/superior direction relative to a patient's head corresponds to moving the soft tissue filter screen in a vertical position relative to the X-ray beam axis.

Also shown in the embodiment of FIG. 5, soft tissue filter screen 550 has a submental-neck portion 500. Submental-neck portion 500 has a leading edge 530 at a position posterior relative to leading edge 520 of anterior facial portion 510. As shown in FIG. 5, the leading edges are lines extending across the entire height of both the anterior facial portion and the submental-neck portion, but the leading edges could be lines extending along part of the height of the portions or lines tangent to the most posterior points of the portions in the event that some of the portions are curved.

Figure 6:
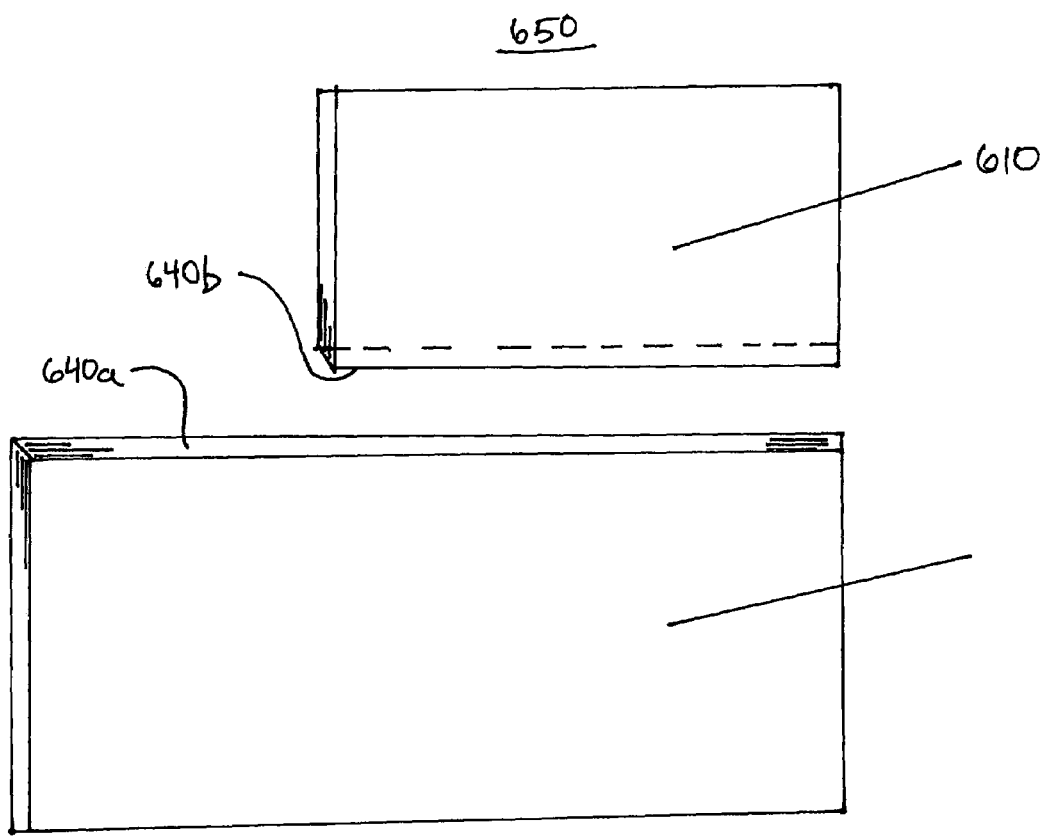
FIG. 6 is a schematic view of a soft tissue filter screen according to another embodiment of the present invention.

Both, the leading edge of the anterior facial portion and the leading edge of the submental-neck portion may be beveled, as shown in FIGS. 5 and 6. A beveled leading edge creates a soft tissue filter screen gradient over which X-rays are attenuated. A beveled edge softens the transition between areas of the radiograph that are exposed to non-attenuated X-rays and areas of the radiograph that are exposed to attenuated X-rays that have passed through the soft tissue filter.

Submental-neck portion 500 is coupled to anterior facial portion 510, meaning that they are connected in some way. According to the embodiment shown in FIG. 5, soft tissue filter screen 550, having anterior facial portion 510 and submental-neck portion 500, is a unitary component. FIG. 6 shows another embodiment of soft tissue filter screen 650 according to the present invention. Soft tissue filter screen 650 is modular in that anterior facial portion 610 and submental-neck portion 600 are separate pieces. While the embodiment in FIG. 6 shows two pieces, any number of individual modular pieces may form the soft tissue filter screen of the present Invention. The modular pieces of soft tissue filter screen, anterior facial portion 610 and submental-neck portion 600, are connected to one another along mated beveled edges 640a and 640b. Alternative connections between the modular pieces may be utilized including slotted engagements, abutted ends and joints filled with other X-ray attenuating materials. Anterior facial portion 610 and submental-neck portion 600 may be held together yet allow movement relative to one another in a conventional manner.

When the soft tissue filter screen of the present invention is a unitary component as shown in FIG. 5, the soft tissue filter screen is independently adjustable relative to the collimator, meaning that it is not immovably affixed to the collimator when the apparatus is in use. The soft tissue filter screen is adjustable relative to the collimator in the anterior/posterior direction as well as in the inferior/superior direction. When the soft tissue filter screen of the present invention is modular as shown in FIG. 6, the soft tissue filter screen 650 is independently adjustable relative to the collimator as described above. In addition, anterior facial portion 610 and submental-neck portion 600 are also each individually adjustable relative to the collimator and relative to one another. For example, submental-neck portion 600 is adjustable relative to anterior facial portion 610 in the anterior/posterior direction. This may be accomplished by having submental-neck portion 600 move in an anterior/posterior direction independently of the anterior facial portion 610 while having the two modular portions move together in the inferior/superior direction. The soft tissue filter screen of FIGS. 5 and 6, while not to scale, is larger than the opening defined by the collimator as shown in FIG. 10A. In this way, the soft tissue filter screen is movable as a unitary component in the inferior/superior direction even when the individual modular components (the anterior facial portion and submental-neck portion) are themselves not adjustable or expandable in the inferior/superior direction relative to one another. In other words, the line of intersection between the two portions can be moved in the inferior/superior direction by moving the entire soft tissue filter screen up and down. Such movement requires that the submental-neck portion 600 (and 500) have sufficient vertical height in its inferior-superior dimension to accommodate different sized heads. This requirement would accommodate for the varying distances between the patient's submental soft tissue and the inferior border of the radiographic image.

The soft tissue filter screen is independently adjustable to the collimator, meaning that the soft tissue filter screen is not movably affixed to the collimator when the apparatus is in use. Any number of known devices are suitable for actuating the adjustment of the unitary soft tissue filter screen relative to the collimator and the modular soft tissue filter screen relative to the collimator and relative to one another. Shown in FIG. 10A is a perspective view of a soft tissue filter screen 1000 according to one embodiment of the present invention as discussed above, coupled with an aperture collimator 1010 also previously discussed. Aperture collimator 1010 defines opening 1020. Soft tissue filter screen 1000 having leading edge 1030 partially covers opening 1020. Shown in FIG. 10A are three actuating adjustment devices 1050. Actuating devices 1050 are ball bearings. FIG. 10B is a side view of FIG. 10A. As can be seen in FIG. 10B, two axial opposing actuating adjustment devices 1050 secure soft tissue filter screen 1000 by frictional fit. The arrows, 1070a and 1070b, represent the forces that secure the soft tissue filter screen in place. While a total of four actuating adjustment devices 1050 are shown, any suitable number of actuating adjustment devices may be used. Actuating adjustment devices 1050 allow soft tissue filter be adjusted in vertical or horizontal directions. In this way, leading edge 1030 of soft tissue filter screen 1000 may cover more of opening 1020 or less of opening 1020. As discussed above, the actuating adjustment devices may be any known conventional device that adjust and positions the soft tissue filter screen in the opening defined by the collimator. Such known devices 1050 may include, but are not limited to servos, pulleys, ball bearings, roller bodies, gears, levers and the like.

Figure 1:
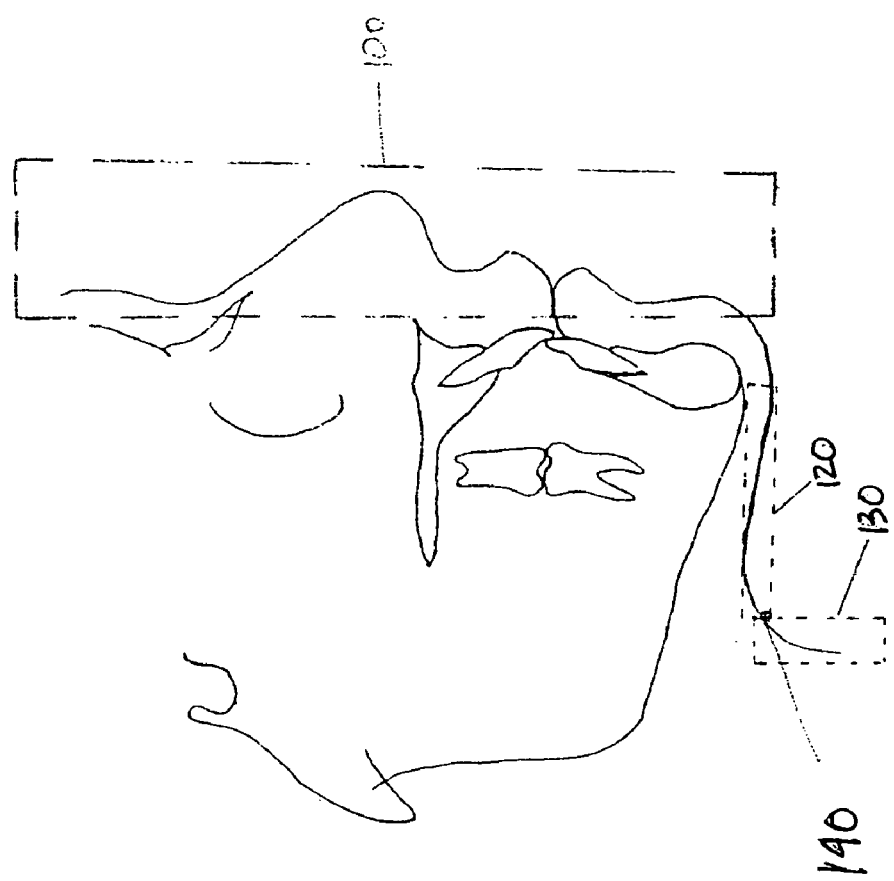
FIG. 1 is a schematic view of a patient's head.
Figure 2A:
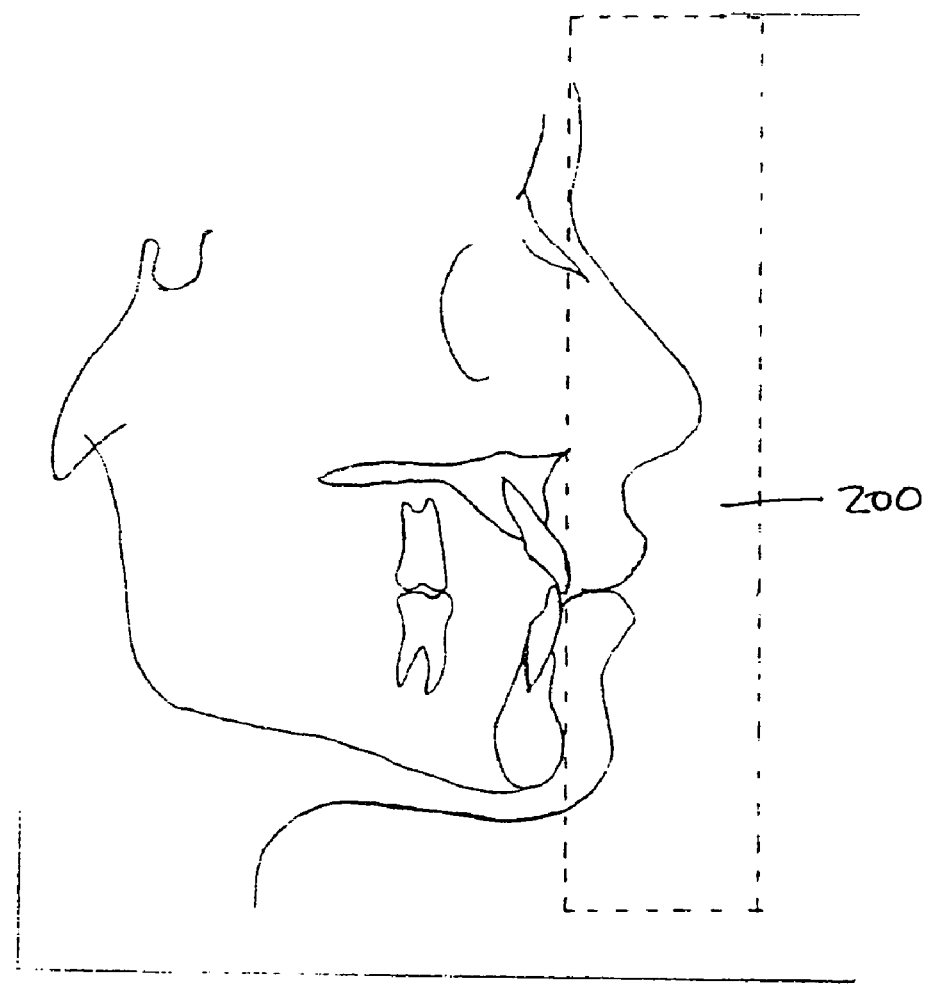
FIG. 2A is a schematic view of the area of a patient's head exposed to attenuated X-rays as a result of a conventional soft tissue filter screen.
Figure 2B:
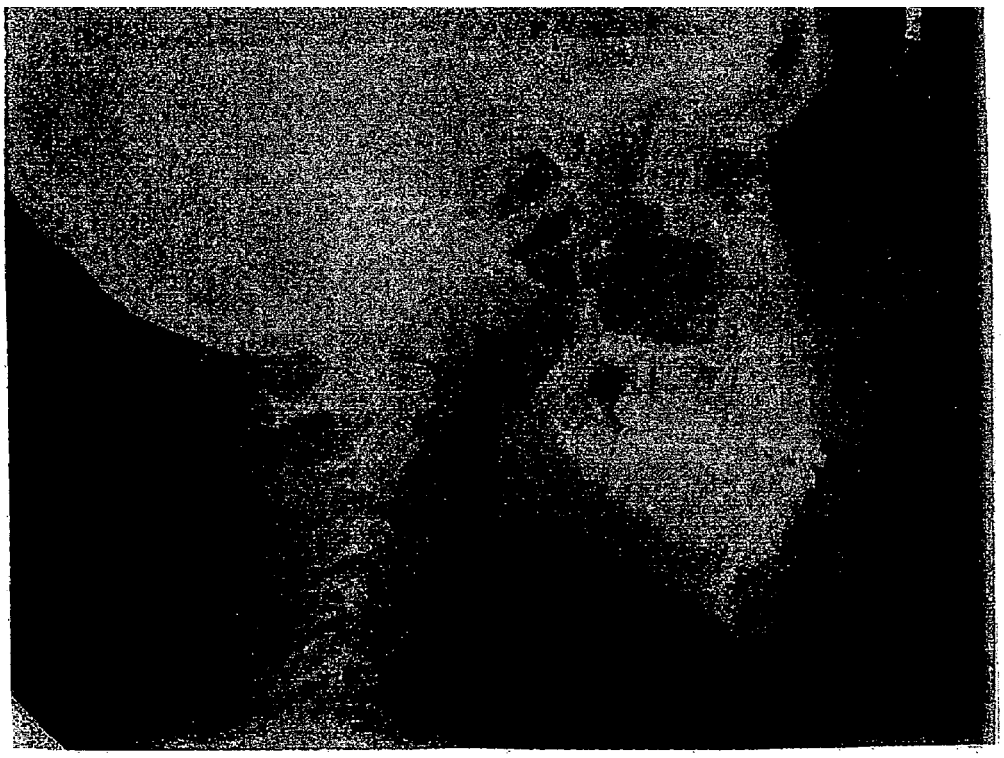
FIG. 2B is a radiograph from a cephalostat using the soft tissue filter screen reflected in FIG. 2A.
Figure 3A:
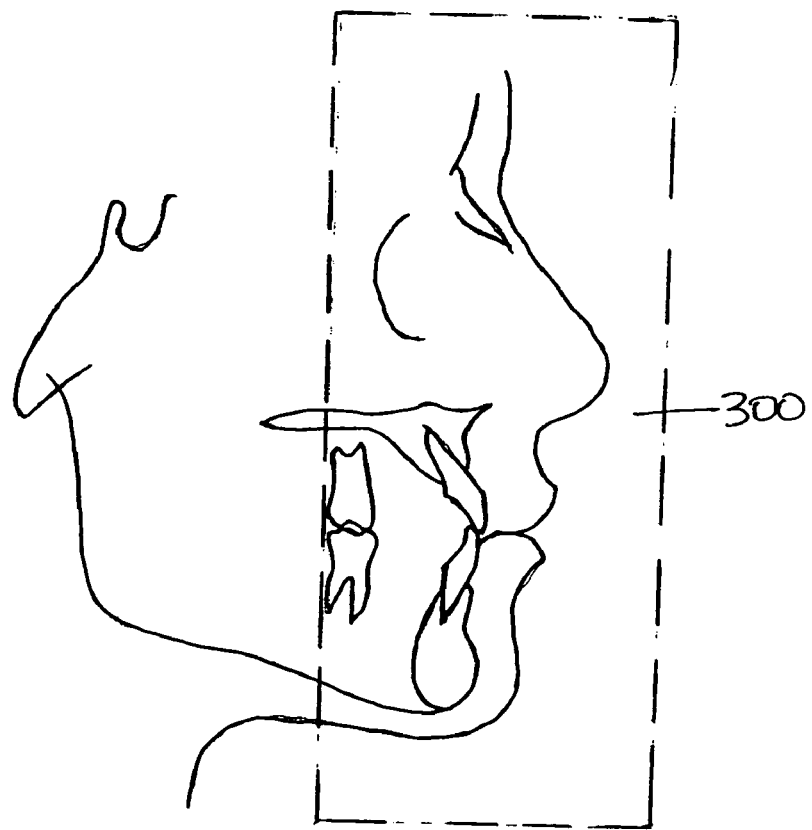
FIG. 3A is a schematic view of the area of patient's head exposed to attenuated X-rays using a conventional soft tissue filter screen at its maximum soft tissue field of view.
Figure 3B:
FIG. 3B is a cephalometric radiograph of a patient's head imaged with the wide soft tissue filter screen reflected in FIG. 3A.
Figure 4A:
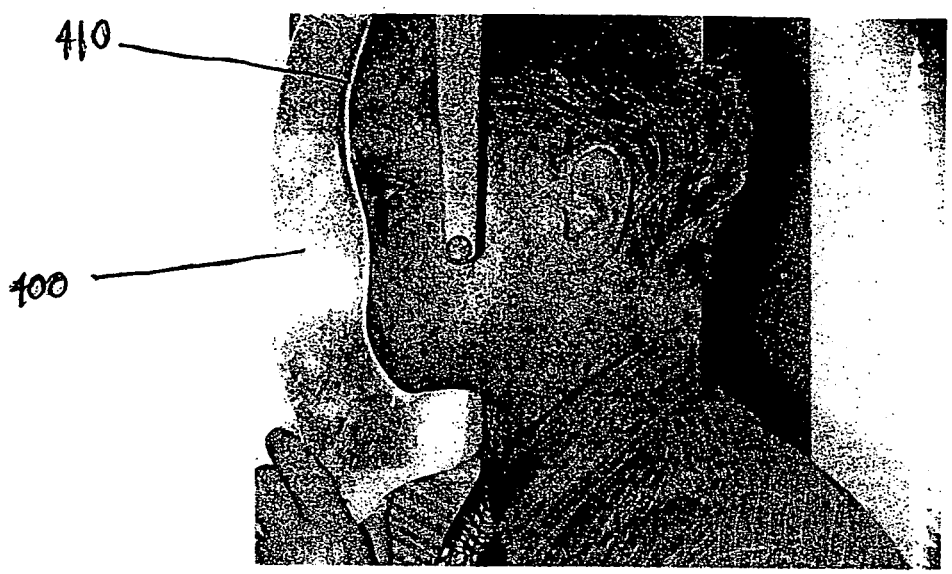
FIG. 4A is a conventional face shield.
Figure 4B:
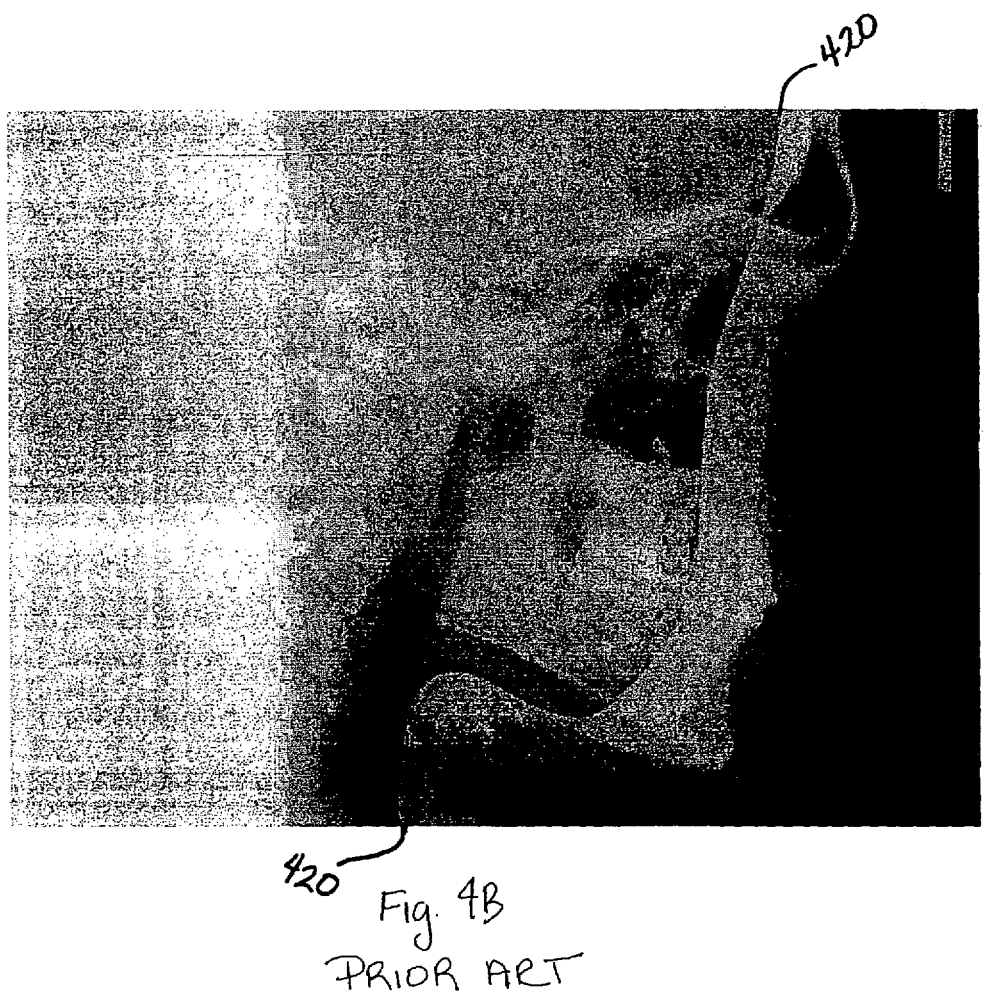
FIG. 4B is a cephalometric radiograph of a person's head using the face shield of FIG. 4A.
Figure 7B:
FIG. 7B is a cephalometric radiograph of a patient's head using the soft tissue filter screen reflected in FIG. 7A.

FIG. 7A shows area 700 of a patient's head exposed to attenuated X-rays using the L-shaped soft tissue filter according to a previously discussed embodiment of the present invention. The outline of area 700 has area 730 corresponding to the anterior facial portion of a soft tissue filter screen and area 740 corresponding to the submental-neck portion of a soft tissue filter screen. Intersection line 750 represents the intersection in the inferior/superior direction of anterior facial portion 510 (or 610) and submental-neck portion 500 (or 600). As can be seen in the resulting radiograph of FIG. 7B, the submental-neck portion of the soft tissue filter screen is adapted to and positioned to enhance radiograph images of the neck contour of a patient (i.e., to attenuate X-rays at points extending from the chin, through the submental-neck portion 120, across cervical point 140, and extending into at least part of the lower neck portion 130 of the patient, as shown in FIG. 1).

Referring to FIG. 8, to align the soft tissue filter screen so that its leading edges will screen X-rays that pass through only the desired soft tissue areas, at least one positioning light 830 identifies an optimum position of the soft tissue filter relative to the head of the patient by emitting a signal representative of the optimum position of the soft tissue filter screen 820. The positioning light 830 is controlled by a controller 840 that is responsive to the signal (as shown by dashed lines 835) and then directs the soft tissue filter screen to move its optimum position, as shown by dashed lines 845. In an alternative embodiment, when the anterior facial portion and the submental-neck portion are modular and adjustable relative to one another, the signal identifies at least three data points. A first data point corresponds to the optimum position for the leading edge of the anterior facial portion. The second data point corresponds to the optimum position for the leading edge of the submental-neck portion. The third data point that corresponds to the optimum position for intersection of the anterior facial portion and the submental-neck portion. In general, the at least one positioning light 830 serves to position the soft tissue filter screen in at least one of the anterior/posterior direction and the superior/inferior direction. The operation of the positioning lights is discussed below.

Shown in FIG. 11 is soft tissue screen system 1100. This soft tissue filter screen system 1100 is for use with a cephalostat having a collimator 1130 for defining an X-ray beam. Collimator 1130 has a housing 1140. Soft tissue filter screen system 1100 includes a soft tissue filter 1150 and a mounting component 1110 supporting soft tissue filter screen 1150 and adapted to be placed adjacent the collimator of the cephalometric radiology apparatus. Shown in FIG. 11, component 1110 supporting soft tissue filter screen 1150 is attached to housing 1140 of the collimator. The soft tissue filter screen of the soft tissue filter screen system may be any one of the numerous embodiments discussed herein above. To attach component 1110 to housing 1140, component 1110 may be adapted with a mounting device. FIG. 1100 shows mounting device as a set of clamps 1120a, 1120b. Alternatively, any other known mounting devices may be used to attached component 1110 to collimator housing 1140. Component 1110 may be attached to collimator housing 1140 as shown in FIG. 11, or component 1110 may be attached directly to the collimator or other suitable structural frame or arm of the cephalometric radiology apparatus to the extent that when mounted, the soft tissue filter screen is positioned in the path of the X-ray beam defined by the collimator.

A radiologist may operate the cephalostat of the present invention having a soft tissue filter screen as described herein and obtain soft tissue and hard tissue images congruently on the same radiograph. The method for using the apparatus involves emitting X-rays from an X-ray source, positioning a collimator across the X-rays to define an X-ray beam, positioning a soft tissue filter screen across the X-ray beam independently of the step of positioning the collimator, and collecting the X-rays on a radiograph. Because the soft tissue filter screen of the present invention is movable independently of the collimator, a radiologist can position the soft tissue filter screen to attenuate the X-rays passing through only that portion of a patient's head in which soft tissue images are desired. More specifically, a radiologist may position the soft tissue filter screen to attenuate X-rays of the patient's forehead, nose, lips, chin and importantly, the facial soft tissue inferior to the mandible and the contour of the patient's neck.

When the radiologist is operating a cephalostat according to one embodiment of the present invention having at least one positioning light, the radiologist may identify an optimum position of the soft tissue filter screen relative to the patient's head. After positioning the patient, the radiologist may direct a positioning light, which may be a laser, to be pointed at the desired location of the edge of the soft tissue filter screen. Once the light is pointed at the desired location, the radiologist then records this point, for example by entering it through a control unit. The cephalostat apparatus then generates a signal representative of that optimum position and communicates it to the soft tissue filter screen. In response, the soft filter screen moves to the optimum position by adjustment in at least one of the anterior/posterior direction and the superior/inferior direction. When, according to another embodiment of the present invention, the anterior facial portion and the submental-neck portion are modular and adjustable relative to one another, the cephalostat generates a signal that identifies at least three data points, in response to movement of the light by the radiologist to the desired points and storing of these points. A first data point corresponds to the optimum position for the leading edge of the anterior facial portion. A second data point corresponds to the optimum position for the leading edge of the submental-neck portion. A third data point corresponds to the optimum position for intersection of the anterior facial portion and the submental-neck portion, along the inferior/superior direction. By identifying the optimum positions of the modular pieces of the soft tissue filter screen, the radiologist can position the soft tissue filter screen within the path of the X-ray beam so that the desired portions of soft tissue in a patient's head are shown without interfering with imaging the hard tissues.

What is claimed:

1. An apparatus for use in a cephalostat comprising:
    a collimator for defining the shape of an X-ray beam;
    a soft tissue filter screen for attenuating a portion of the X-ray beam, wherein the soft tissue filter screen comprises:
      a) an anterior facial portion having a leading edge, wherein the leading edge is located at the most posterior position of the anterior facial portion, and
      b) a submental-neck portion coupled to the anterior facial portion and having a leading edge at a position posterior relative to the leading edge of the anterior facial portion,
    wherein the soft tissue filter screen is independently adjustable relative to the collimator.

2. An apparatus according to claim 1, wherein the soft tissue filter screen is L-shaped having a first leg and a second leg disposed perpendicular to one another, wherein the anterior facial portion is the first leg and the submental-neck portion is the second leg.

3. An apparatus according to claim 1, wherein the soft tissue filter screen is adjustable relative to the collimator in the anterior/posterior direction.

4. An apparatus according to claim 1, wherein the soft tissue filter screen is adjustable relative to the collimator in the superior/inferior direction.

5. An apparatus according to claim 1, wherein the anterior facial portion and the submental-neck portion comprise a unitary component.

6. An apparatus according to claim 1, wherein the leading edge of the anterior facial portion and the leading edge of the submental-neck portion are beveled.

7. An apparatus according to claim 1, wherein the anterior facial portion and the submental-neck portion are modular.

8. An apparatus according to claim 7, wherein the submental-neck portion is adjustable relative to the anterior facial portion in the anterior/posterior direction.

9. An apparatus according to claim 7, wherein the anterior facial portion and the submental-neck portion are connected to one another along mated beveled edges.

10. An apparatus according to claim 1, wherein the submental-neck portion is adapted to enhance radiograph images of the neck contour of a patient.

11. An apparatus according to claim 1, wherein the soft tissue filter screen is copper.

12. An apparatus according to claim 1, wherein the collimator comprises four plates defining an opening to define the X-ray beam, wherein the plates are independently adjustable relative to one another towards and away from the center of the opening.

13. An apparatus according to claim 1, wherein the collimator comprises a single frame defining an opening to define the X-ray beam.

14. A cephalometric radiology apparatus comprising
    a support structure;
    an X-ray source supported by the support structure for emitting X-rays;
    a collimator supported by the support structure and positioned along the path of the X-rays for defining an X-ray beam emitted from the X-ray source;
    a soft tissue filter screen for attenuating a portion of the X-ray beam and mounted independently of the collimator, wherein the soft tissue filter screen comprises:
      a) an anterior facial portion having a leading edge, wherein the leading edge is located at the most posterior position of the anterior facial portion, and
      b) a submental-neck portion coupled to the anterior facial portion and having a leading edge at a position posterior relative to the leading edge of the anterior facial portion,
    wherein the soft tissue filter screen is independently adjustable relative to the collimator; and
    an X-ray detector to collect X-rays emitted from the X-ray source.

15. An apparatus according to claim 14 further comprising at least one positioning light to identify an optimum position of the soft tissue filter relative to the head of the patient, wherein said positioning light emits a signal representative of the optimum position, and a controller responsive to the signal for moving the soft tissue filter screen to the optimum position.

16. An apparatus according to claim 15, wherein the anterior facial portion and the submental-neck portion are modular and adjustable relative to one another, and the signal identifies a first data point corresponding to the optimum position for the leading edge of the anterior facial portion, a second data point corresponding to the optimum position for the leading edge of the submental-neck portion, and a third data point corresponding to the optimum position for intersection of the anterior facial portion and the submental-neck portion.

17. An apparatus according to claim 15, wherein the at least one positioning light positions the soft tissue filter screen in at least one of the anterior/posterior direction and the superior/inferior direction.

18. An apparatus according to claim 14, wherein the soft tissue filter screen is mounted between the collimator and the X-ray source.

19. An apparatus according to claim 14, wherein the collimator is mounted between the soft tissue filter screen and the X-ray detector.

20. A method for imaging soft tissue and hard tissue congruently on the same radiograph comprising the steps of:
    emitting X-rays from an X-ray source;
    positioning a collimator across the X-rays to define an X-ray beam;
    positioning a soft tissue filter screen across the X-ray beam independently of the step of positioning the collimator, to attenuate the X-rays passing through a portion of the forehead, nose, lips, chin and neck of a patient, wherein the soft tissue filter screen comprises:
      a) an anterior facial portion having a leading edge, wherein the leading edge is located at the most posterior position of the anterior facial portion, and b) a submental-neck portion coupled to the anterior facial portion and having a leading edge at a position posterior relative to the leading edge of the anterior facial portion; and collecting the X-rays on a radiograph.

21. A method according to claim 20 further comprising:

identifying an optimum position of the soft tissue filter screen; and generating a signal representative the optimum position, wherein the step of positioning the soft tissue filter screen comprises receiving the signal and moving the soft tissue filter screen to the optimum position by adjusting the soft tissue filter screen in at least one of the anterior/posterior direction and the superior/inferior direction.

22. A method according to claim 21, wherein the anterior facial portion and the submental-neck portion are modular and adjustable relative to one another, and the signal identifies a first data point corresponding to the optimum position for the leading edge of the anterior facial portion, a second data point corresponding to the optimum position for the leading edge of the submental-neck portion, and a third data point corresponding to the optimum position for intersection of the anterior facial portion and the submental-neck portion.

23. A modular soft tissue filter screen system for use with a cephalostat having a collimator for defining an X-ray beam, which system comprises:

a soft tissue filter screen for attenuating a portion of the X-ray beam, wherein the soft tissue filter screen comprises:

a) an anterior facial portion having a leading edge, wherein the leading edge is located at the most posterior position of the anterior facial portion, and b) a submental-neck portion coupled to the anterior facial portion and having a leading edge at a position posterior relative to the leading edge of the anterior facial portion, and a mounting component supporting the soft tissue filter screen and adapted to be attached to the cephalostat at a position such that the soft tissue filter screen is aligned within the X-ray beam.

24. A system according to claim 23, wherein the soft tissue filter screen is L-shaped having a first leg and a second leg disposed perpendicular to one another, wherein the anterior facial portion is the first leg and the submental-neck portion is the second leg.

25. A system according to claim 23, wherein the soft tissue filter screen is adjustable in the anterior/posterior direction relative to the collimator.

26. A system according to claim 23, wherein the anterior facial portion and the submental-neck portion are modular.

27. A system according to claim 26, wherein the submental-neck portion is adjustable relative to the anterior facial portion in the anterior/posterior direction.

28. A system according to claim 26, wherein the anterior facial portion and the submental-neck portion are connected to one another along mated beveled edges.

29. A system according to claim 23, wherein the anterior facial portion and the submental-neck portion comprise a unitary component.

30. A system according to claim 23, wherein the leading edge of the anterior facial portion and the leading edge of the submental-neck portion are beveled.

31. A system according to claim 23, wherein the soft tissue filter screen is adjustable relative to the collimator in a inferior/superior direction.

32. A system according to claim 23, wherein the submental-neck portion is adapted to enhance radiographic images of the facial soft tissue inferior to the mandible and the neck contour of a patient.

33. A system according to claim 23, wherein the soft tissue filter screen is copper.

34. A modular soft tissue filter screen system according to claim 23 further comprising a housing for the collimator, wherein the mounting component for the soft tissue filter screen is adapted to be attached to the housing of the collimator.

* * * * *